(12) United States Patent
Weaver et al.

(10) Patent No.: US 8,272,343 B1
(45) Date of Patent: Sep. 25, 2012

(54) FINGERPRINT GOGGLES

(76) Inventors: David E. Weaver, Lookout, WV (US); Mason Hines, Oak Hill, WV (US)

(*) Notice: Subject to any disclaimer, the term of this patent is extended or adjusted under 35 U.S.C. 154(b) by 905 days.

(21) Appl. No.: 12/350,811

(22) Filed: Jan. 8, 2009

Related U.S. Application Data

(63) Continuation of application No. 12/206,692, filed on Sep. 8, 2008, now abandoned, which is a continuation-in-part of application No. 11/564,605, filed on Nov. 29, 2006, now Pat. No. 7,487,739.

(60) Provisional application No. 61/010,455, filed on Jan. 8, 2008, provisional application No. 61/010,462, filed on Jan. 9, 2008, provisional application No. 61/010,491, filed on Jan. 8, 2008, provisional application No. 60/967,945, filed on Sep. 7, 2007, provisional application No. 60/817,167, filed on Jun. 27, 2006, provisional application No. 60/740,953, filed on Nov. 29, 2005.

(51) Int. Cl.
*A61B 5/117* (2006.01)
*G06K 9/00* (2006.01)
*F21V 21/08* (2006.01)
*C23C 16/00* (2006.01)

(52) U.S. Cl. ....... 118/31.5; 118/715; 382/124; 362/103; 362/230; 362/231; 362/555; 436/164

(58) Field of Classification Search .......... 118/31.5, 118/715; 382/100, 124, 125; 362/103, 105, 362/108, 230, 231, 555, 106, 58; 436/71, 436/164

See application file for complete search history.

(56) References Cited

U.S. PATENT DOCUMENTS

| | | | | |
|---|---|---|---|---|
| 4,119,369 A * | 10/1978 | Eloranta et al. | ................. | 351/49 |
| 4,297,383 A | 10/1981 | Bourdon | | |
| 4,504,408 A * | 3/1985 | Morton | ................... | 252/301.16 |
| 4,556,579 A | 12/1985 | Lowell | | |
| 4,613,515 A | 9/1986 | Reggio | | |
| 4,708,882 A * | 11/1987 | Asano et al. | ...................... | 427/1 |
| 4,794,260 A * | 12/1988 | Asano et al. | ............... | 250/458.1 |
| 5,172,256 A * | 12/1992 | Sethofer et al. | ................ | 349/14 |
| 5,266,112 A | 11/1993 | Crosbie | | |
| 5,281,293 A | 1/1994 | Frame et al. | | |
| 5,342,645 A | 8/1994 | Eisele et al. | | |
| 5,348,759 A | 9/1994 | Weaver et al. | | |
| 5,395,445 A | 3/1995 | Bohanan | | |
| 5,424,092 A | 6/1995 | Weaver et al. | | |
| 5,906,871 A | 5/1999 | Takebe et al. | | |
| 6,423,946 B1 | 7/2002 | Berka et al. | | |
| 6,660,054 B2 | 12/2003 | Manna et al. | | |
| 6,865,285 B1 * | 3/2005 | Villa-Aleman | ............... | 382/124 |
| 7,323,207 B2 | 1/2008 | Nichols et al. | | |
| 7,487,739 B1 * | 2/2009 | Weaver et al. | ............... | 118/31.5 |

(Continued)

FOREIGN PATENT DOCUMENTS

JP 2-268744 2/1990

(Continued)

*Primary Examiner* — Jeffrie R Lund
(74) *Attorney, Agent, or Firm* — Thompson Hine LLP

(57) ABSTRACT

An apparatus and method for developing latent fingerprints having a heat source and sublimation system wherein the sublimation system is in communication with the heat source. Upon activating the heat source, the heat transforms a cyanoacrylate and a sublimation dye of the sublimation system into vapor. The vapor contacts an object to reveal any latent fingerprints on the object. A light source excites the sublimation dye causing photoluminescent emissions which are viewed through filter goggles.

20 Claims, 13 Drawing Sheets

U.S. PATENT DOCUMENTS

| | | | |
|---|---|---|---|
| 2004/0184660 A1* | 9/2004 | Treado et al. | 382/191 |
| 2005/0057797 A1* | 3/2005 | Treado et al. | 359/368 |
| 2005/0252444 A1* | 11/2005 | Nichols et al. | 118/31.5 |
| 2006/0126168 A1* | 6/2006 | Treado et al. | 359/385 |
| 2007/0026130 A1 | 2/2007 | Arndt | |
| 2010/0047433 A1* | 2/2010 | Shimoda et al. | 427/1 |
| 2010/0143575 A1* | 6/2010 | Knaggs | 427/1 |
| 2010/0265320 A1* | 10/2010 | Treado et al. | 348/61 |

FOREIGN PATENT DOCUMENTS

WO     WO 94/26166     11/1994

\* cited by examiner

600

700

800

900

1100

1600

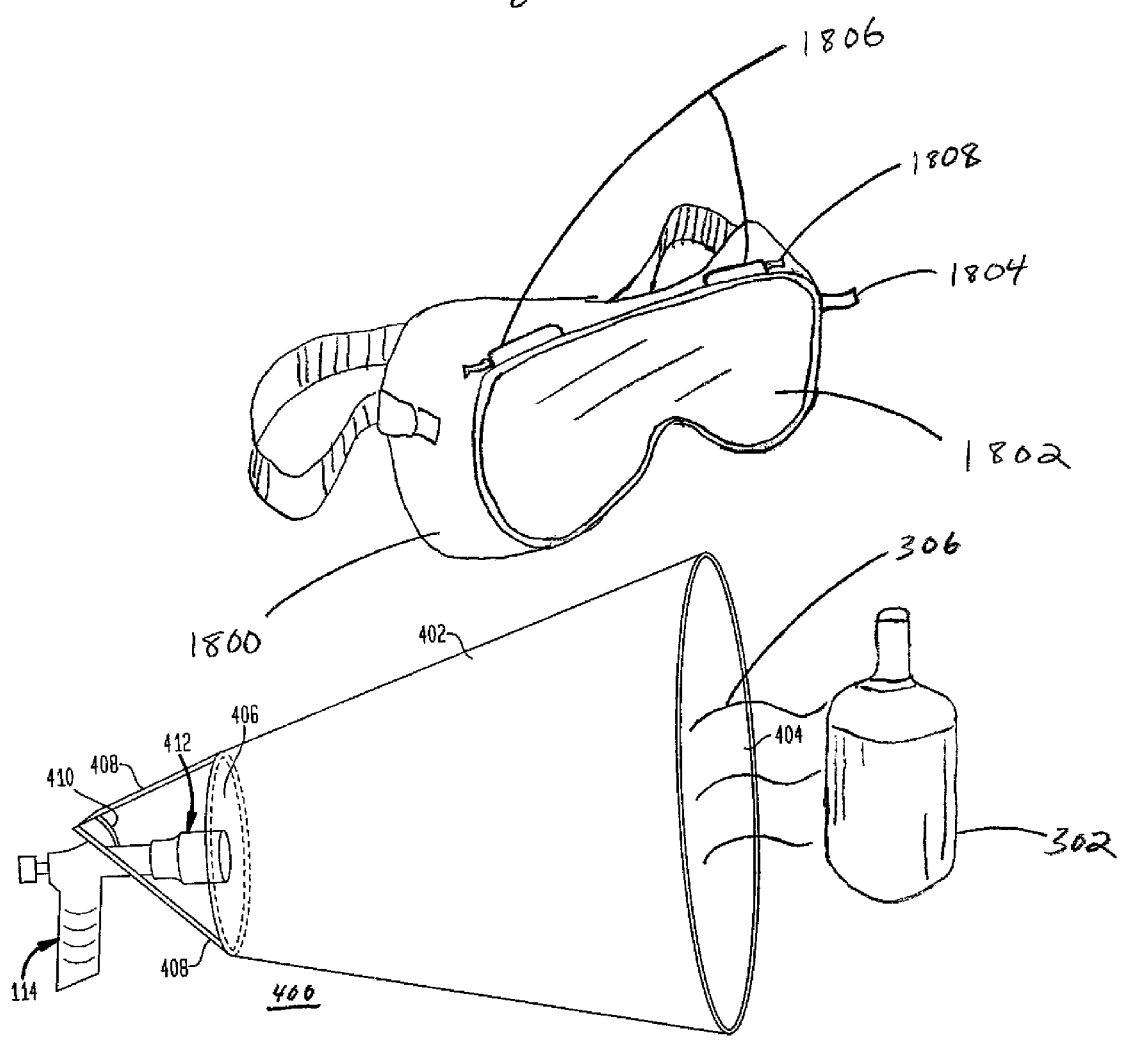

FINGERPRINT GOGGLES

CROSS-REFERENCE TO RELATED APPLICATION

This application claims the benefit of U.S. Provisional Application No. 61/010,455 filed Jan. 8, 2008, and is a continuation in part of U.S. Nonprovisional application Ser. No. 12/206,692 filed Sep. 8, 2008, which claims the benefit of U.S. Provisional Application No. 61/010,462 filed Jan. 9, 2008, U.S. Provisional Application No. 61/010,491 filed Jan. 8, 2008 and U.S. Provisional Application No. 60/967,945 filed on Sep. 7, 2007 and is a continuation in part of U.S. Nonprovisional application Ser. No. 11/564,605 filed Nov. 29, 2006.

This work was supported at least in part by the National Institutes of Justice (NIJ) under NIJ grant number 2007-DN-BX-K242. Accordingly, the United States government may have certain rights herein.

BACKGROUND

1. Technical Field

The present invention relates to apparatuses for developing latent fingerprints and the method of use thereof, and in particular, to the use of a chamber in combination with a heat source and a sublimation system containing a mixture of cyanoacrylate and a sublimation dye wherein the application of heat transforms the mixture of cyanoacrylate and sublimation dye to vapor. In one embodiment, the vapor is circulated with a vapor circulating device which results in the quick and efficient development of latent fingerprints on objects contained in the chamber. In other aspects, a light source excites the sublimation dye causing photoluminescent emissions which are observable when viewed through an optical filter that in one aspect is integral with the chamber itself. In another aspect, the chamber includes a thermo cycling apparatus and a humidifying apparatus to recharge or rehydrate latent fingerprints.

2. Related Art

The primary component of a fingerprint is water—approximately 98%—which evaporates readily from a fingerprint and leaves a residue of various chemicals. The residue contains both inorganic and organic materials some of which can remain detectable on a surface long after the water component of the perspiration has evaporated. These chemicals include water soluble amino acids, peptides, salts, glucose, lactic acid, ammonia, riboflavin, and water insoluble oils and other sebaceous secretions (generally referred to as lipids). For the purposes of this application, the term "fingerprint" is used to describe the chemical residue left when a person touches an object, and/or the image formed by the residue.

The use of cyanoacrylate in the development of latent fingerprints on objects is well known and has been used as such for many years. Specifically, it is the reaction of the cyanoacrylate monomer and a catalyst that creates a microcrystalline vapor which adheres to fingerprints. Once the vapor cures, the cyanoacrylate forms a white polymer substance that reveals the fingerprint. To further enhance the detection of latent fingerprints, the cyanoacrylate monomer is mixed with dyes, specifically sublimation dyes, which upon excitation produce photoluminescent emissions. Such a mixture is disclosed in U.S. Provisional Application No. 61/010,491 entitled "Sublimation Dye Stained Co-Polymerization Cyanoacrylate," which is hereby incorporated herein in its entirety.

U.S. Pat. No. 4,556,579 to Lowell discloses a kit for developing latent fingerprints wherein liquid cyanoacrylate monomer is deposited onto a porous fiber plug made of cellulose acetate fibers. The resulting fumes from the chemical reaction generate any latent fingerprints that come into contact with the fumes. The kit also has a solvent for removing such fingerprints when desired.

Similar to the '579 patent, U.S. Pat. No. 4,613,515 to Reggio also discloses a kit for developing latent fingerprints on a solid surface. The kit contains an absorbent pad impregnated with a cyanoacrylic polymerization catalyst and one or more initiators, a promoter and an accelerator. The kit also provides a separate source of a polymerizable alpha-cyanoacrylate monomer with at least one inhibitor agent. In operation, a cyanoacrylate monomer is added to the surface of the pad and the pad is placed adjacent a surface believed to contain a fingerprint. The pad remains undisturbed until it generates a microcrystalline vapor from the reaction of the cyanoacrylic catalyst and monomer. The vapor travels through the air to the solid surface wherein upon contact with the surface it adheres to the latent fingerprint, thereby making the latent fingerprint visible.

There are several disadvantages with the kits of the '579 and '515 patents. The user must physically add the cyanoacrylate monomer to a pad or plug which may result in unwanted spillage or a wrong amount of cyanoacrylate monomer applied to the pad. The kits also consist of multiple components which increases the complexity of using the kits as well as increases the amount of waste.

U.S. Pat. No. 5,342,645 to Eisele, et al. discloses a metal cartridge containing a porous or fibrous pad such as steel or glass wool, impregnated with a cyanoacrylate ester and a volatile, emissive lanthanide metal-complex or actinide metal-complex. Upon the application of heat, e.g., a butane-powered torch, the chemical reaction produces a chemical vapor that is used to develop latent fingerprints. The principal disadvantages with the '645 patent is that it requires a heat resistent housing and the use of a butane torch, both requirements making the cartridge clumsy and potentially dangerous to use. Further, the metal complex does not fully integrate into the polymer matrix, resulting in a vapor that is easily wiped off the developed fingerprint, making the transportation of delicate evidence difficult.

U.S. Pat. Nos. 5,348,759 and 5,424,092 to Weaver, et al. discloses a device for developing latent fingerprints. The device has a housing that contains a cyanoacrylate (either in liquid or solid form) and is adapted to receive a propane torch. Upon lighting the torch, the cyanoacrylate is vaporized and propelled toward the object to be tested on which any latent fingerprints appear within minutes. The user may replace the cyanoacrylate as needed for new tests. The disadvantage with these devices is that they require the use of a propane torch which increases the potential danger of using the devices. The devices also have multiple components including the need for additional cyanoacrylate to refill the housing, which increases the maintenance of the devices.

U.S. Pat. No. 5,395,455 to Bohanan discloses a method and apparatus for developing latent fingerprints on a portion of skin. The apparatus uses a heater to create a cyanoacrylate vapor which is propelled by a fan through a hose and comes in contact with skin. As seen in previous devices, this apparatus is very cumbersome to carry and use in field operation, and requires the use of a separate heater and fan which increases the maintenance effort.

U.S. Pat. No. 6,423,946 to Berka, et al. discloses an apparatus for developing latent fingerprints having a sealable container for depositing objects being tested for fingerprints. The container has an electrical heater as well as an exhaust means for evacuating air from the internal chamber. In operation, the method includes heating the container, placing objects within the chamber, adding a few drops of cyanoacrylate on an upper surface of an internal receptacle, covering the container, and pumping air from the container. After the fumes have developed any latent fingerprints on the objects within the chamber, the cover is removed and the objects are taken out. The disadvantage with the '946 device is that it is cumbersome to carry and use in the field. The user requires an electrical outlet for powering the heater. Also, the internal size of the chamber limits the number, size, and shape of the objects that can be placed in the container for testing.

Therefore, upon review of the prior art, there is a need for a simple, self-contained, re-chargeable apparatus for developing and visualizing latent fingerprints. There is a further need for such an apparatus to be mobile and easy to use, and having a containment system for directing the fumes or vapors toward and around the object being examined. There is a further need to enhance the detection of fingerprints by illumination of the developed fingerprints in combination with an optical filter to enhance the visibility of the illuminated fingerprints. The enhanced visibility offered by the current apparatus allows active monitoring of the polymerization process to ensure proper development levels to prevent overdevelopment, which can ruin the clarity of the fingerprint. There is a need to rehydrate or recharge dehydrated fingerprints in preparation for fingerprint development.

BRIEF DESCRIPTION OF THE DRAWINGS

The present invention is described with reference to the accompanying drawings. In the drawings, like reference numbers indicate identical or functionally similar elements. Additionally, the left-most digit(s) of a reference number identifies the drawings in which the reference number first appears.

FIG. 18 is a perspective view of an apparatus of the present invention.

DETAILED DESCRIPTION OF THE INVENTION

In the photoluminescent visualization of latent fingerprints, the latent fingerprint is exposed to one or more chemical reagents which react with compounds in the latent print to form a product capable of photoluminescence. The image of the latent print is then viewed or photographed with the aid of an optical filter and under illumination of light of appropriate wavelength to cause excitation which results in photoluminescent emissions from the chemical reagents deposited on the fingerprint.

Figure 1:
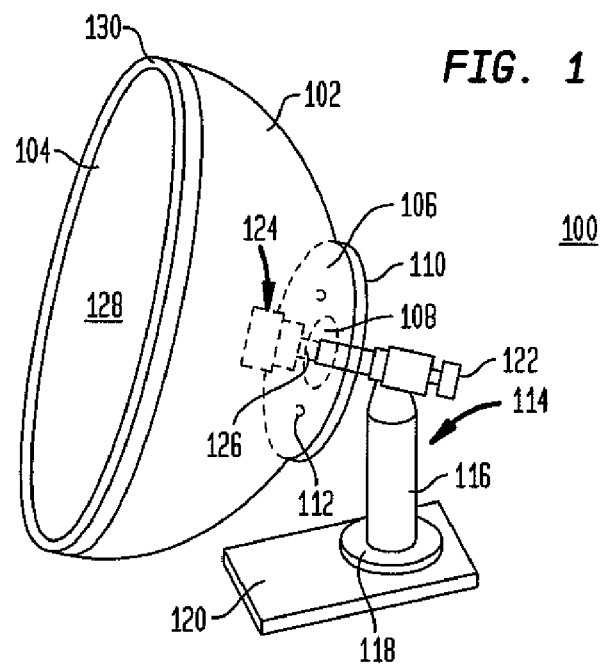
FIG. 1 is a perspective view of an apparatus of the present invention.

FIG. 1 shows one aspect of the present invention, namely an apparatus 100 having a heat source 114, a sublimation system 124, and a chamber 102. The heat source 114 has a heat emitting end 126 that is in communication with the internal space 128 of the chamber 102, and preferably extends into the internal space 128. The sublimation system 124 is in communication with the heat emitting end 126 of the heat source 114, and preferably is removably attached to the heat emitting end 126.

In the preferred embodiment, the heat source 114 is a commercially available pressurized fuel system, such as a butane canister fuel system, having a handle 116 for storing a pressurized can of butane fuel, an on/off button 122, and a first base 118 affixed to a larger second base 120 which is sized such that the apparatus 100 stands in a substantially upright position when the second base 120 is placed on a level surface. The heat emitting end 126 of the heat source 114 is joined to the handle 116 such that expelled fuel from the can of pressurized fuel flows through and exits from the heat emitting end 126 of the heat source 114 in an ignited/heated state. In operation, a user places a can of pressurized fuel in the handle 116, and upon activating the on/off button 122, a flame, or heat, is expelled from the heat emitting end 126.

The use of a pressurized fuel system as the heat source 114 is for convenience only. It would be readily apparent to use alternative heat sources 114, such as, any replaceable fuel canister system, a torch system, a forced air heat system, an exothermic chemical reaction, an electric heat system with an attached fan or any other means for creating vapor, as would be understood by a person having ordinary skill in the art.

Figure 2A:
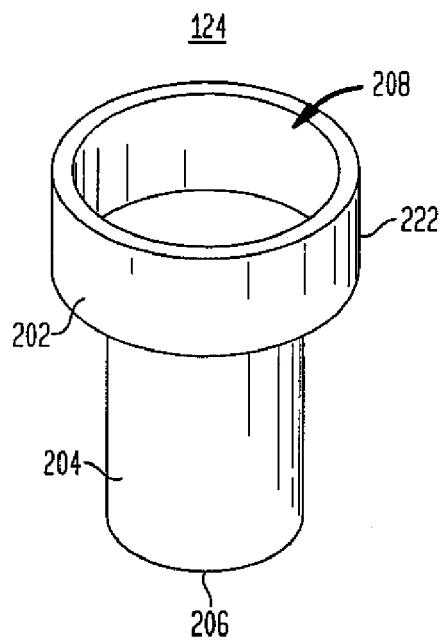
FIG. 2A is a perspective view of sublimation cartridge of the present invention.
Figure 2B:
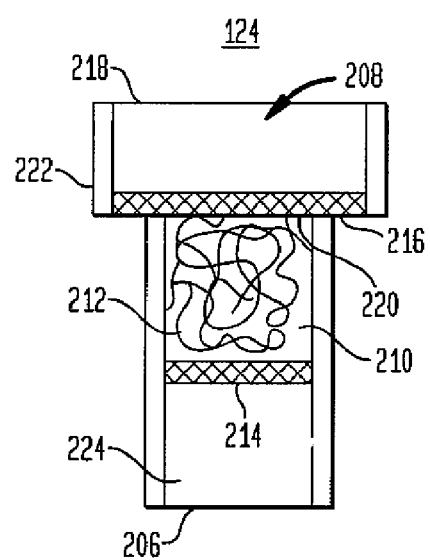
FIG. 2B is a planar cut-away cross sectional view of the sublimation cartridge.

The preferred sublimation system 124 is shown in greater detail in FIGS. 2A and 2B. In the preferred embodiment, the sublimation system 124 is a hollow sublimation cartridge 222 having a first end 218, a second end 206, a head 202, a head cavity 208, a throat 204, and a throat cavity 210 wherein the diameter of the head cavity 208 is greater than the diameter of the throat cavity 210. The first end 218 of the sublimation cartridge 222 is in communication with the internal space 128 of the chamber 102, and in the preferred embodiment, the first end 218 of the sublimation cartridge 222 is disposed within the internal space 128 of the chamber 102.

The sublimation cartridge 222 is preferably made of metal, ceramic, or glass and is about 1-2 inches in length. The sublimation cartridge 222 contains the components needed to create the cyanoacrylate vapors 306 used in developing latent fingerprints. In this first embodiment, a porous pad 212, such as a ball of steel wool, ceramic fiber, granulated loose wool, and non-granulated loose wool, is disposed within the throat cavity 210 between a first retaining screen 216 and a second retaining screen 214. The first and second retaining screens 216, 214 are preferably made of bronze metal, but this is for convenience wherein any high temperature resistance material is suitable. The first retaining screen 216 is positioned at the intersection 220 of the head 202 and throat 204, whereas the second retaining screen 214 is positioned at a point within the throat 204. The positioning of the first retaining screen 216 and the second retaining screen 214 are also for convenience.

A mixture of liquid cyanoacrylate and sublimation dye is deposited on the porous pad 212 and allowed to dry. The second end 206 of the sublimation cartridge 222 is sized such that it slides onto the heat emitting end 126 of the heat source 114 and is pressure fit to stay in place during transport and use of the apparatus 100. There is sufficient distance 224 between the second end 206 of the sublimation cartridge 222 and the second retaining screen 214 such that the sublimation cartridge 222 stays on the heat emitting end 126 of the heat source 114. Also, the attachment of the sublimation cartridge 222 to the heat emitting end 126 is such that it provides the proper air flow to reduce the possibility of an explosion and maintain combustion for those embodiments utilizing a combustion based heat source 114.

Figure 11:
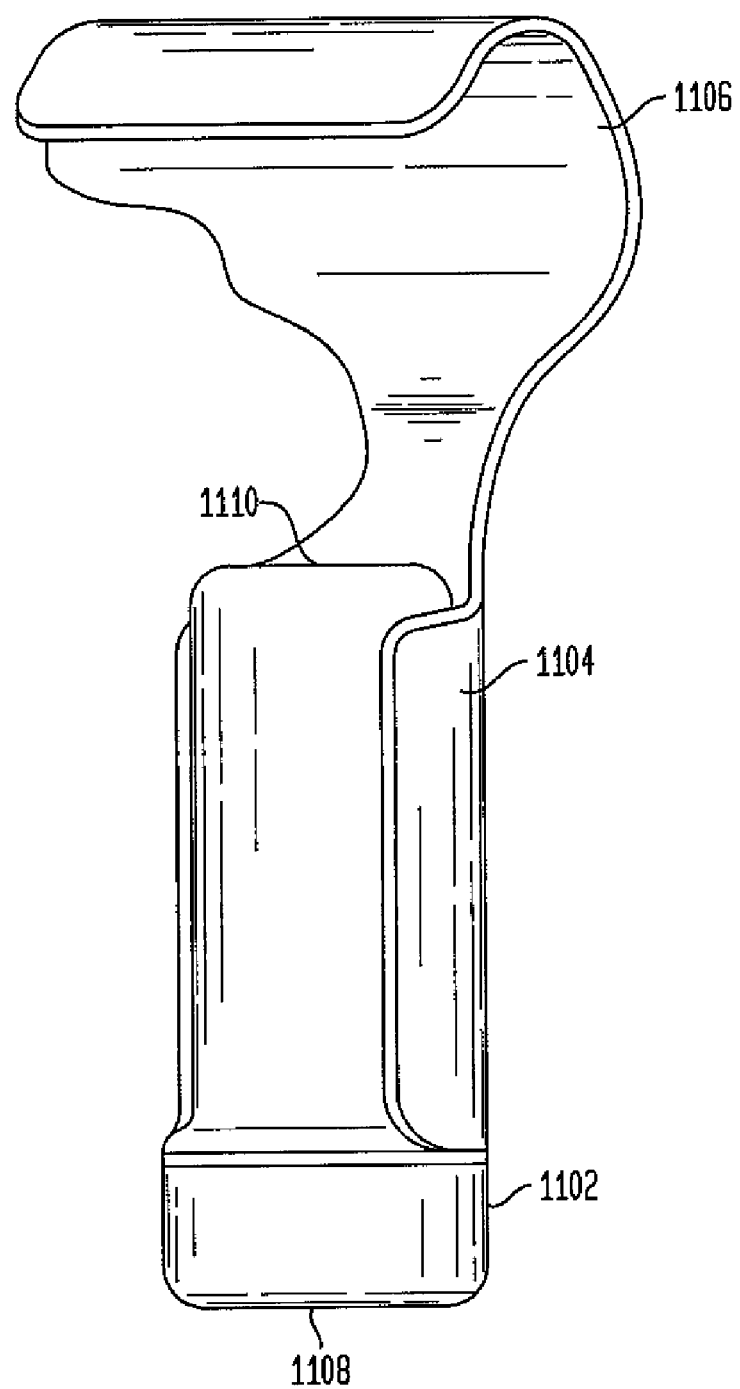
FIG. 11 is a front view of an alternative sublimation cartridge.
Figure 12:
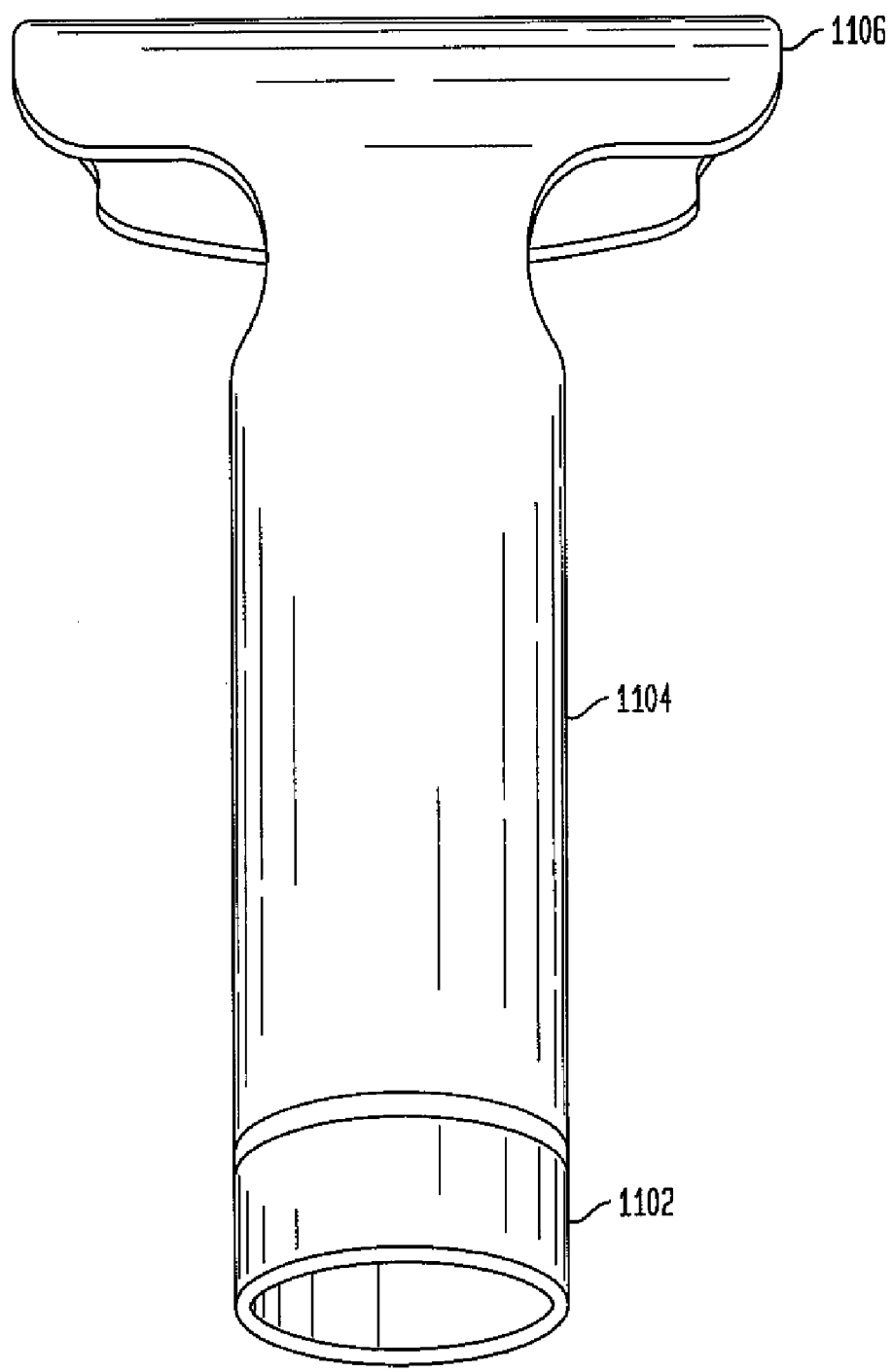
FIG. 12 is a back view of an alternative sublimation cartridge.

In another embodiment, shown in FIG. 11, the sublimation cartridge 1100 contains a sublimation adaptor 1102, made of metal or any other suitable high temperature resistant material. Sublimation adaptor 1102 comprises of a hollow cylinder adapted to receive, with a friction fit, a sublimation cartridge 1104. Sublimation cartridge 1104 contains a cavity 1106 adapted to receive the mixture of cyanoacrylate and sublimation dye. The first end 1108 of the sublimation adaptor 1100 is sized such that it slides onto the heat emitting end 126 of the heat source 114. FIG. 12 is an alternative view of sublimation adaptor 1102.

Figure 13:
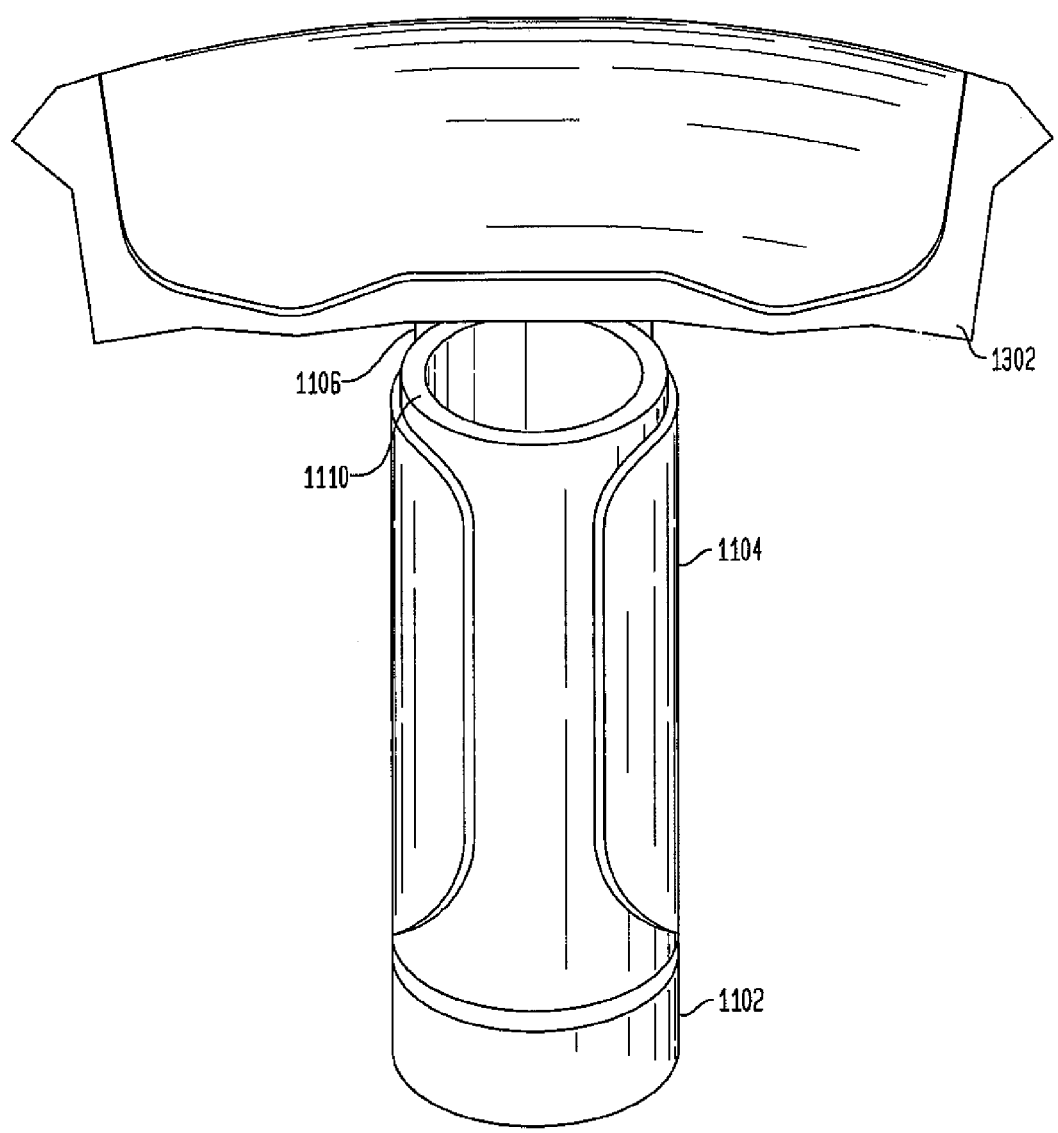
FIG. 13 is a front view of an alternative sublimation cartridge.
Figure 14:
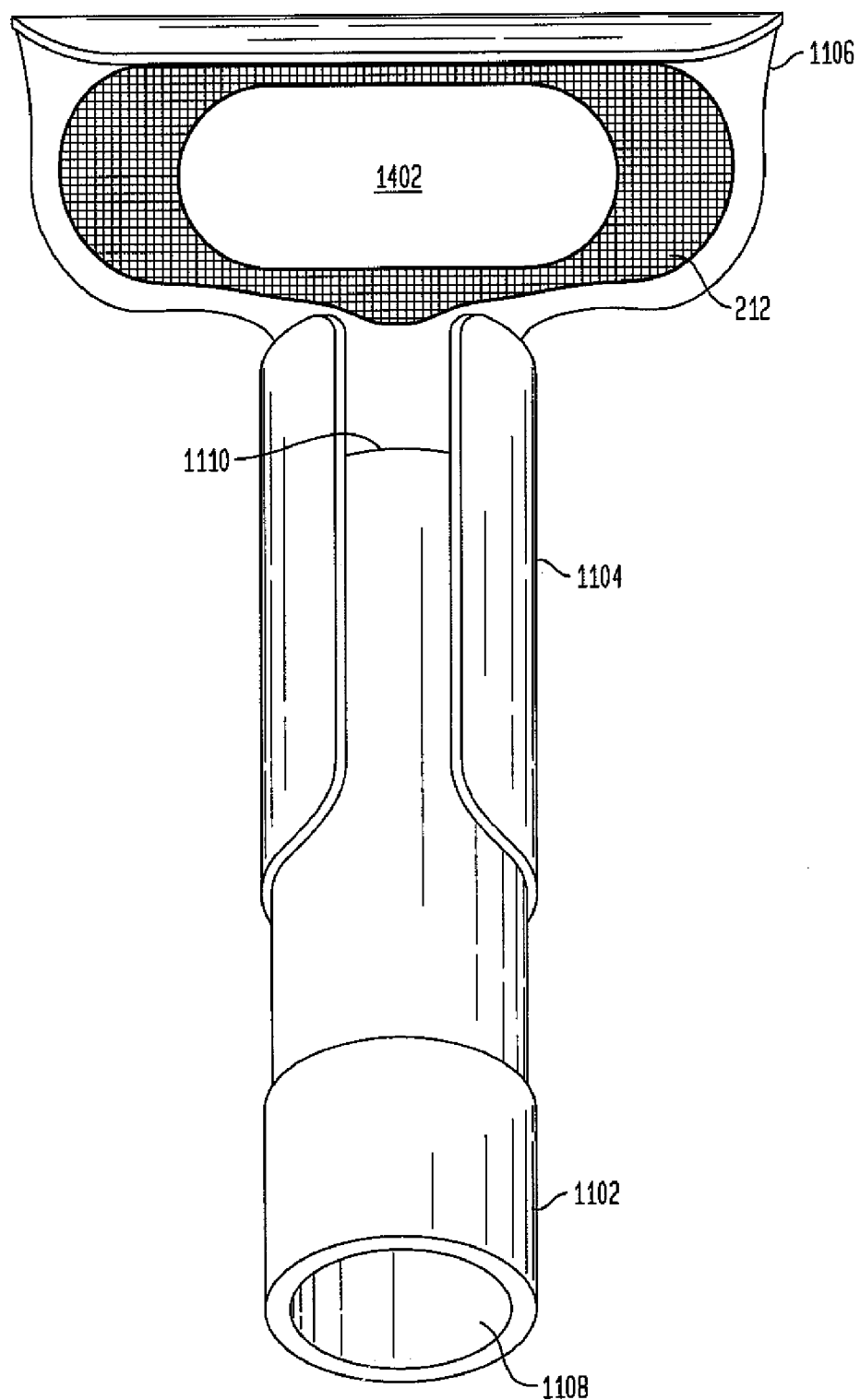
FIG. 14 is a front view of an alternative sublimation cartridge.

The second end 1110 of sublimation adaptor 1102 funnels heat from heat source 114 to activate the mixture of cyanoacrylate and sublimation dye which, in one embodiment, is embedded on a casing 1302, as depicted in FIG. 13. Casing 1302 is made from a suitable material which can withstand high temperatures, such as aluminum foil, and is attached to the exterior of cavity 1106 as shown in FIG. 13. Alternatively, in another embodiment shown in FIG. 14, porus pad 212, such as a ball of steel wool, ceramic fiber, granulated loose wool, and non-granulated loose wool, is deposited within cavity 1106. A mixture of liquid cyanoacrylate and liquid sublimation dye is deposited on the steel wool pad 1402 and allowed to dry.

In the first embodiment, the chamber 102 is a transparent plastic dome, about 11 inches in diameter, defining an internal space 128 and having an open end 104 and a connecting end 106 which is used to connect the chamber 102 to the heat source 114. The chamber 102 may have rigid or flexible walls and edges. As shown in FIG. 1, the connecting end 106 has an entry aperture 108 through which the heat emitting end 126 of the heat source 114 protrudes into the internal space 128 of the chamber 102. A back plate 110, preferably made of metal or heavy duty plastic, is securely mounted to the connecting end 106 of the chamber 102 by one or more removable screws 112 or other mechanical fasteners. The back plate 110 in turn is securely mounted on the heat emitting end 126 of the heat source 114, thereby joining the chamber 102 to the heat source 114. The chamber 102 is shown and described as a transparent dome for convenience purpose only. It would be readily apparent to one of ordinary skill in the art to design and, implement a chamber 102 having a different shape and size, and to removably attach a chamber 102 to a heat source 114.

In a second embodiment, the chamber 102 has a seal 130 around the perimeter edge of the open end 104. The seal 130 functions to further contain the vapors 306 within the internal space 128 by sealing the open end 104 against a surface on which the object 302 being examined is placed. The seal 130 is made of a foam or neoprene type material. Possible surfaces on which to use the apparatus 100 include the ground, a wall, furniture surface, vehicle surface, and the like.

Figure 10:
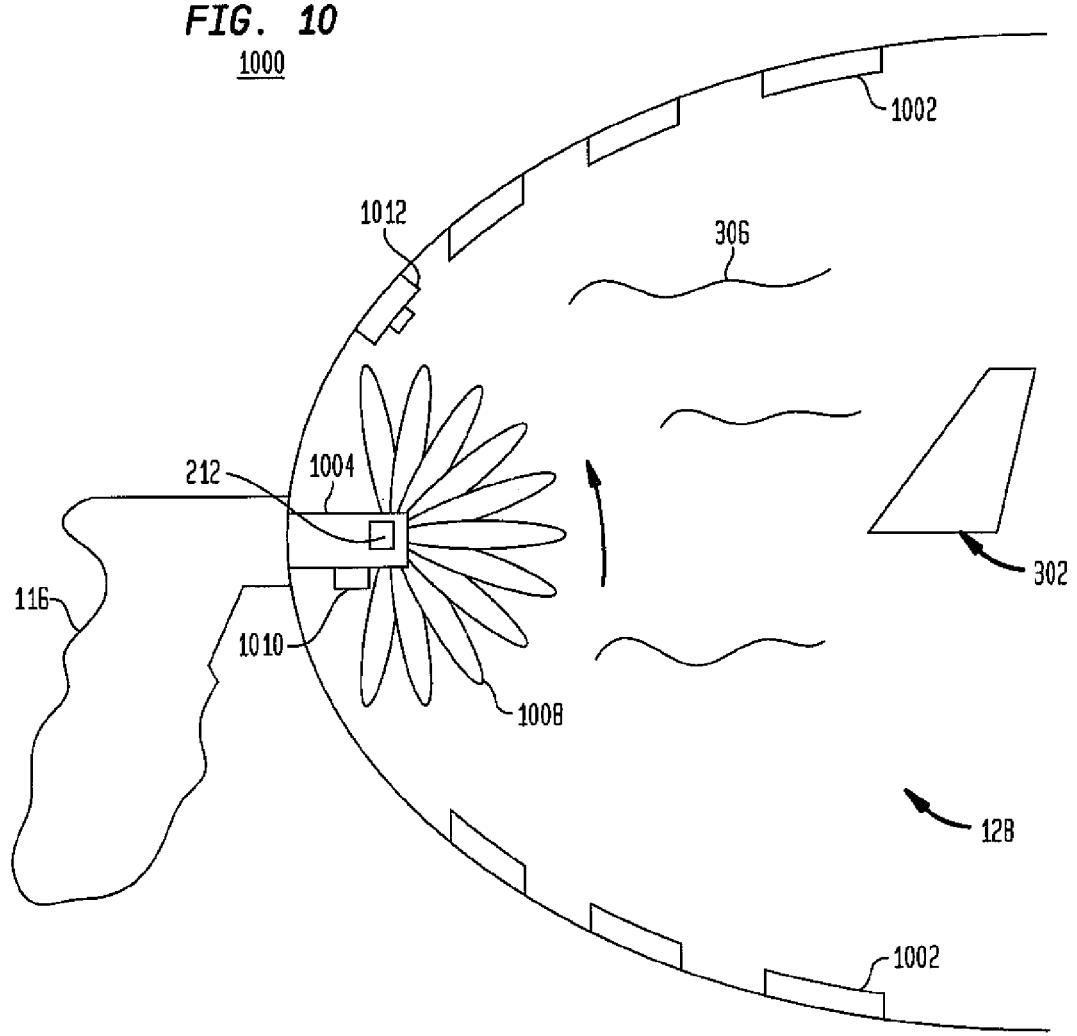
FIG. 10 is a sectional view of an alternative embodiment of the apparatus for developing latent fingerprints on an object.

In a third embodiment, the chamber 102 further comprises a source of radiation, more generally referred to as a light source 1002, as shown in FIG. 10, which emits light into the chamber 102 and generally toward the object 302. Light as used herein encompasses the entire electromagnetic spectrum. Non-limiting examples of light sources 1002 include light emitting diodes, fluorescent bulbs, incandescent bulbs, lasers, filtered arc lamps, ultraviolet light source, infra red light source or any combination thereof, or any other means for emitting radiation or more generally light, as would be understood by a person having ordinary skill in the art. In one embodiment the light source 1002 or means of emitting light is connected, attached or otherwise affixed onto an interior surface of chamber 102. In another embodiment the light source 1002 emits light in a range from about 415 nm to about 505 nm. In still another embodiment, the light source 1002 emits a substantial portion of its light in a range from about 415 nm to about 505 nm. In still another embodiment, the light source 1002 emits substantially all of its light within a +/−10 nm range of a wavelength selected from between 415 nm and 505 nm. In one embodiment the light source 1002 is a light emitting diode (LED), and in still another embodiment the light source 1002 is a blue LED emitting light between a range of about 450 nm and 470 nm.

In another embodiment, the light source 1002 has variable wavelength functionality and emits light in at least one of the following ranges: ultra violet spectrum, visible light spectrum or the infra-red spectrum. In one embodiment, the light source 1002 emits a substantial portion of its light in at least one of the following ranges: about 75 nm to about 380 nm, about 380 nm to about 450 nm; about 450 nm to about 495 nm; about 495 nm to about 570 nm; about 570 nm to about 590 nm; about 590 nm to about 620 nm, about 620 nm to about 750 nm, about 750 nm to about 1500 nm, about 1500 nm to about 3000 nm and about 3000 nm to about 10,000 nm. In yet another embodiment, the light source 1002 emits the majority of its radiation within +/−10 nm range of 450 nm.

In one embodiment the light source 1002 is adapted to excite or stimulate a response from the sublimation dye that is contained in vapors 306. As used herein, a dye forms any kind of molecular bond, including covalent, ionic, Van der Waals etc., with any component of the residue of fingerprints directly or via the cyanoacrylate, including amino acids, peptides, lipids and oils. Non-limiting examples of dyes include: ninhydryn, 5-methoxyninhydryn, 4-chloro-7-nitrobenzofurazan (NBD)-chloride, 1-8 diazafluorene-9-one (DFO), aminoninhydryns and 5-thioninhydryns, rhodamine 6G, ardrox, basic yellow 40 and yellow 43.

In one embodiment, dyes suitable for the sublimation dye include dyes which emit photoluminescent radiation (i.e. photoluminescent emissions) upon excitation by a light source 1002. Photoluminescence is a process in which a substance absorbs photons (electromagnetic radiation) and then re-radiates photons. This can be described as an excitation to a higher energy state and then a return to a lower energy state accompanied by the emission of a photon. The output can be one of many forms of luminescence; non-limiting examples include resonant radiation, fluorescence and phosphorescence. In one embodiment, the photoluminescent emissions occur at a range within the ultra violet spectrum, visible light spectrum or in the infra-red spectrum.

In one embodiment, the photoluminescent emissions occur in at least one of the following ranges: about 75 nm to about 380 nm, about 380 nm to about 450 nm, about 435 nm to about 445 nm, about 450 nm to about 495 nm, about 495 nm to about 570 nm, about 515 nm to about 540 nm, about 570 nm to about 590 nm, about 590 nm to about 620 nm, about 620 nm to about 750 nm, about 750 nm to about 1000 nm, about 1000 nm to about 1250 nm, about 1250 nm to about 1500 nm, about 1500 to about 3000 nm, and about 3000 nm to about 10,000 nm.

In another embodiment, the dyes are sublimation dyes mixed in solution with cyanoacrylate and optionally with glacial acetic acid, variable ratios of thixotropic gel and variable ratios of electrolyte components, to keep the sublimation dye and cyanoacrylate in solution. The combination of these ingredients in solution provide a shelf life stable liquid product, that when heated through various means and imported into enclosed chambers, vehicles, or rooms of crime scene provides vapors, which includes cyanoacrylate vapor and sublimation dye vapor, which preferentially adheres to fingerprint ridge deposits, including the residue components.

In a fourth embodiment, an optical filter is integral with chamber 102 to pass photoluminescent emissions produced by the sublimation dye after excitation from a light source while attenuating light not associated with the photoluminescent emissions. In one embodiment, chamber 102 is an optical filter made of amber colored acrylic plastic which attenuates scattered blue excitation light to further enhance the detection of the photoluminescent emission from the developed fingerprint. In another aspect, optical filter inserts (not shown) are incorporated into the chamber 102 structure.

Chamber 102, in this fourth embodiment, operates, in part, as an optical filter that is placed between the detector or observer and the photoluminescent emissions. Chambers, goggles and any other means for filtering photoluminescent emissions as would be understood by a person having ordinary skill in the art can be employed. In one embodiment chamber 102 is constructed from a colored transparent acrylic plastic such as Acrylite® amber (Cyro#436-4 GP or Chemeast #2422) available from CYRO Industries. Non-limiting examples of colored acrylic plastic include yellow, blue, green, red, bronze, gray, pink and burgundy.

In a fifth embodiment, the chamber 102 is in communication with a vapor circulating device 1008. A vapor circulating device 1008 is any device which circulates vapors 306 which aids in surrounding the object 302 with vapors 306 resulting in an increase in the rate of fingerprint development. The vapor circulating device 1008 facilitates the equal distribution of vapor and helps increase the rate of evaporation of water from the fingerprint. The cooling effect also extends the window of the polymerization event of the mixture of cyanoacrylate and sublimation dye resulting in increased fingerprint development.

Non-limiting examples of a vapor circulating device 1008 include fans, blowers, rotating walls, swirlers, and other means of enhancing the circulation or directing of vapors 306 in the vicinity of and around the object 302 as would be understood by a person having ordinary skill in the art. In one embodiment, vapor circulating device 1008 is a micro-fan positioned on the interior of chamber 102. In another embodiment the vapor circulating device 1008 is an external blower in communication with the chamber 102 which is used to circulate vapors 306. In still another embodiment, the vapor circulating device 1008 is a fan that is mounted within the enclosed volume of the apparatus 100 such that the air and vapors 306 contained within the volume of the chamber 102 are in motion.

In another embodiment a small sponge 1010 with a mixture of water and ammonia is placed behind the fan to promote development of fingerprints. Alternatively, a glacial acetic acid mixture is deposited on the sponge 1010 to promote the development of fingerprints.

In one embodiment, a capture device 1012 for capturing or photographing the latent fingerprint is incorporated or attached to chamber 102. Capture device 1012, captures the resulting photoluminescent product after excitation of the dye with a light source. In one embodiment, capture device 1012 is an imaging device, such as a camera of variable wavelength functionality capable of capturing the entire electromagnetic spectrum including ultraviolet, visible and infrared. In another embodiment, the capture device 1012, is a digital imager tuned with enhanced sensitivity to the emission or scattering frequencies generated by the sublimation dye in response to the light source 1002. In still another aspect, the capture device 1012 has an integral filter that is tuned to attenuate emission frequencies that are not associated with the sublimation dye in response to light source 1002.

Figure 3:
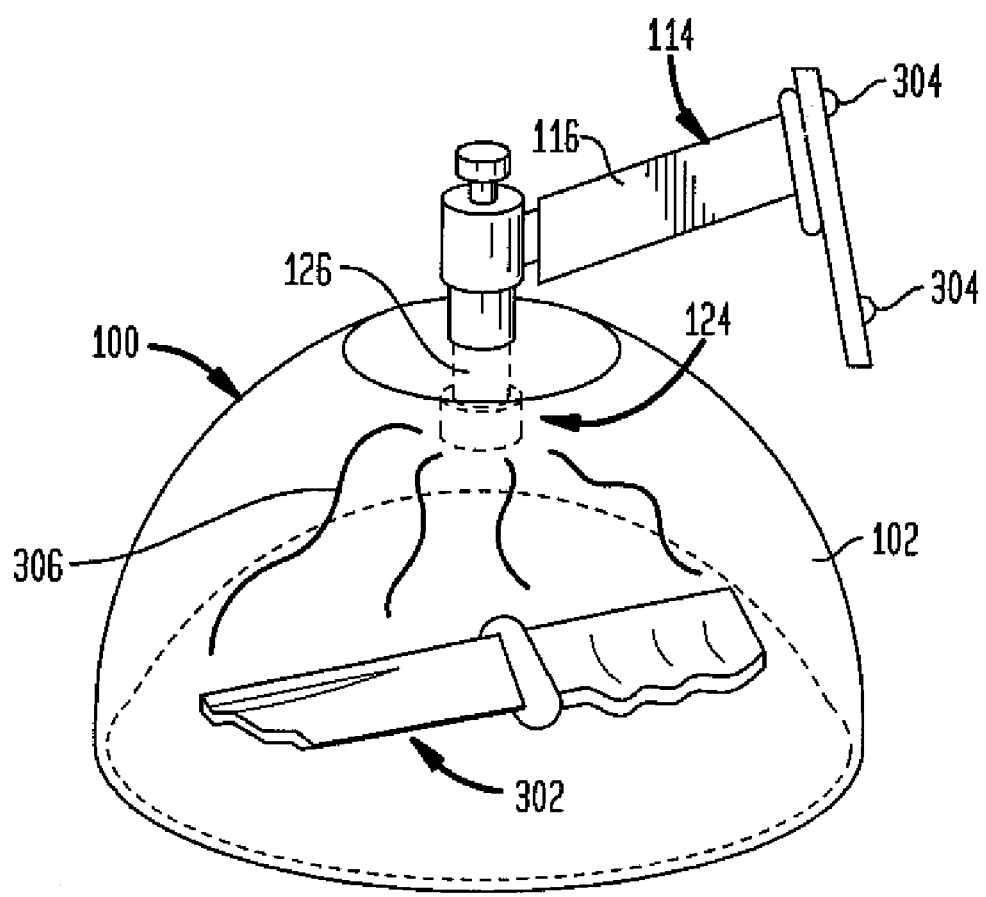
FIG. 3 is a perspective view of the apparatus for developing latent fingerprints on an object.

The use and operation of the apparatus 100 is shown in FIG. 3. A user turns the on/off button 122 to activate the heat source 114 which causes the generation of heat out of the heat emitting end 126 of the heat source 114. The heat activates the cyanoacrylate disposed on the porous pad 212 which in turn generates the cyanoacrylate vapors 306. The user holds the heat source 114 by the handle 116 and places the chamber 102 over the object 302, such as a weapon (knife) or other item, being examined. Latent fingerprints start to develop within seconds because the chamber 102 contains the vapors 306 within the internal space 128 and directs the vapors 306 directly toward and around the object 302. When finished developing fingerprints on the object 302, the user returns the apparatus 100 to the resting position on the second base 120 as shown in FIG. 1.

The use and operation of an alternative embodiment of the present invention is the illuminated apparatus 1000, which includes elements from apparatus 100, as shown in FIG. 10. A user (not shown) activates the heat source 1004 which causes the generation of heat. The heat activates the mixture of cyanoacrylate and sublimation dye disposed on the porous pad 212 which in turn generates vapors 306, which is comprised of both cyanoacrylate and sublimation dye vapors. The user holds the heat source 1004 by the handle 116 and places the chamber 102 over the object 302, such as a weapon (knife) or other item, being examined. The vapors 306 containing cyanoacrylate and sublimation dye attach to or "develop" the latent fingerprints. The user then activates the light source 1002. In the embodiment depicted, multiple light sources 1002 are used in combination. In other embodiments, a single light source 1002 is used to emit light. In still other embodiments, a single light source 1002 with a broad light spectrum in combination with selectable filters are used to excite the sublimation dye on the object 306. In the embodiment shown in FIG. 10, the user also activates the vapor circulating device 1008. Latent fingerprints start to develop within seconds because chamber 102 contains the vapors 306 within the internal space 128 in proximity with the object 306. In one embodiment, a vapor circulating device 1008 redirects vapors 306 toward and around the object 302. The photoluminescent emissions associated with the sublimation dye enhances the visibility of the developed fingerprints which are observed by viewing through chamber 102. Alternatively, the photoluminescence is captured by the capture device 1012.

As a non-limiting example, a blue LED emitting light at a range of about 450 nm+/−10 nm is used in conjunction with a sublimation dye of yellow dye 43. When the blue light illuminates and thereby excites yellow dye 43, photoluminescence occurs at a range of about 515 nm to about 540 nm. Amber colored optical filters, attenuates unwanted scattered excitation light from the blue LED as well as other light sources not associated with the photoluminescence from yellow dye 43. As would be understood by a person having ordinary skill in the art, the photoluminescent emissions spectra of the dye dictates the excitation spectra of light required as well as the type of optical filter to attenuate any unwanted light.

The sublimation cartridge 222 of this first embodiment is rechargeable in that once the cyanoacrylate is exhausted, more cyanoacrylate and in some embodiments the sublimation dye is deposited on the porous pad 212. Preferably, the user deposits about 6-7 drops of liquid cyanoacrylate onto the porous pad 212 through the first retaining screen 216. The cyanoacrylate may be applied to the porous pad 212 while the sublimation cartridge 222 is still connected to the heat emitting end 126 of the heat source 114, or alternatively, after the sublimation cartridge 222 is removed from the heat source 114. Regardless of how the cyanoacrylate is applied to the sublimation cartridge 222, the sublimation cartridge 222 should be in a vertical position while depositing the cyanoacrylate to prevent the cyanoacrylate from dripping off of the porous pad 212 during its drying time. After approximately three minutes of drying, the apparatus 100 is ready to use again. If the sublimation cartridge 222 was removed for the application of new cyanoacrylate, it is slide back onto the heat emitting end 126 of the heat source 114 prior to use. A recharged sublimation cartridge 222 provides approximately five to ten minutes of fingerprint developing capabilities.

Figure 4:
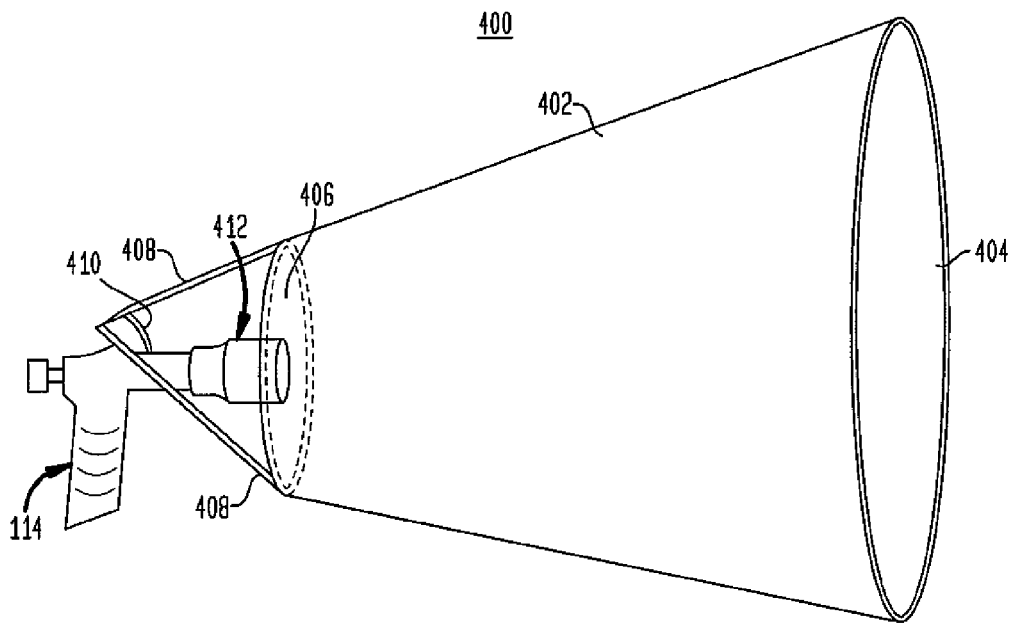
FIG. 4 is a perspective view of an alternative embodiment of the apparatus.
Figure 5:
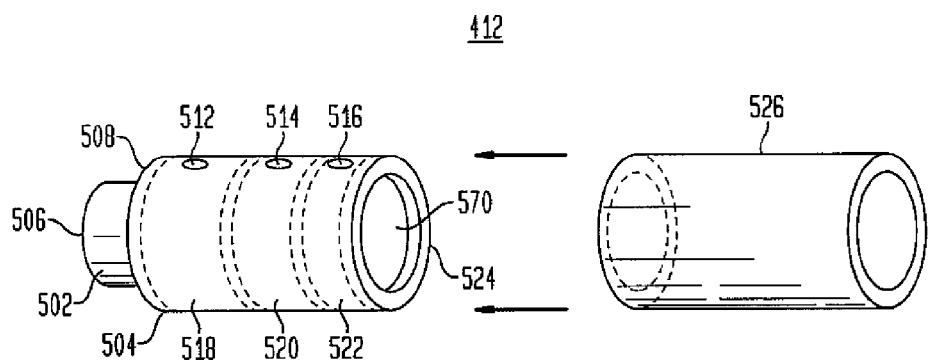
FIG. 5 is a perspective view of an alternative sublimation cartridge.

In a second embodiment, the sublimation system 124 is a sublimation cartridge 412 shown in FIGS. 4 and 5. In this embodiment, the sublimation cartridge 412 is an elongated hollow tube 504, defining an internal space 510, with a first end 524 adapted to be in communication with the internal space 128 of the chamber 402, and a second end 506 adapted to be removably secured to the heat emitting end 126 of the heat source 114. In one embodiment, the second end 506 is sized to be slidably attachable to the heat emitting end 126 of the heat source 114. However, in alternative embodiments, conventional connectors and/or mechanical fasteners may be used to removably secure the sublimation cartridge 412. In another alternative embodiment, as shown on FIG. 5, the sublimation cartridge 412 also has a connector portion 502 at the second end 506 which is sized and shaped to be removably mounted to the heat emitting end 126 of the heat source 114. The connector portion 502 is a smaller hollow tube having a diameter adapted to be pressure fit on the heat emitting end 126.

The sublimation cartridge 412 also has a plurality of apertures, such as first aperture 512, second aperture 514, and third aperture 516, extending through the wall of the sublimation cartridge 412 and into the internal space 510. Preferably, the first aperture 512, the second aperture 514, and the third aperture 516 are aligned along a longitudinal axis of the sublimation cartridge 412.

In one embodiment, three elements are disposed within the internal space 510 of the sublimation cartridge 412. A first element 518 is adapted for receiving and retaining water through the first aperture 512. A second element 520 is adapted for receiving and retaining a cyanoacrylate, such as a liquid or solid heat activated cyanoacrylate, through the second aperture 514. A third element 522 is adapted for receiving and retaining a sublimation dye through the third aperture 516. The three elements 518, 520, and 522 may be disposed within the internal space 510 in any order, but the described order is preferred. Also, it would be readily apparent to one of ordinary skill in the art to determine the amount of water, cyanoacrylate and sublimation dye to use with the present invention.

The sublimation cartridge 412 is preferably made of metal, ceramic, certain plastics that can withstand high temperatures, or glass. Also, the second element 520 and the third element 522 are preferably porous pads such as steel wool, ceramic fiber, granulated loose wool, or non-granulated loose wool. The first element 518 is preferably a porous insulating pad such as a ceramic insulating fire brick which can withstand high temperatures.

Upon charging the sublimation cartridge 412 with water, cyanoacrylate, and a sublimation dye, the sublimation cartridge 412 is mounted on the heat emitting end 126 of the heat source 114 as shown in FIG. 4. Also, an optional sleeve cover 526 may be slid over the sublimation cartridge 412 to further support the sublimation cartridge 412 and to cover the first, second and third apertures 512, 514, 516. A chamber 102 as shown in FIG. 1 may be used with this embodiment, or alternatively, an alternative chamber 402 is used.

In an alternative embodiment, a chamber 402 having an open end 404 and an entry aperture 406 is mounted to the heat source 114 by one or more tethers 408 attached to a flange 410 on the heat source 114 such that the first end 524 of the sublimation cartridge 412 is directly in front of, or alternatively extends into, the entry aperture 406 of the chamber 402. In operation, upon activating the heat source 114, the heat engages the sublimation cartridge 412 which generates the vapor 306 used to develop latent fingerprints as described herein.

Figure 6:
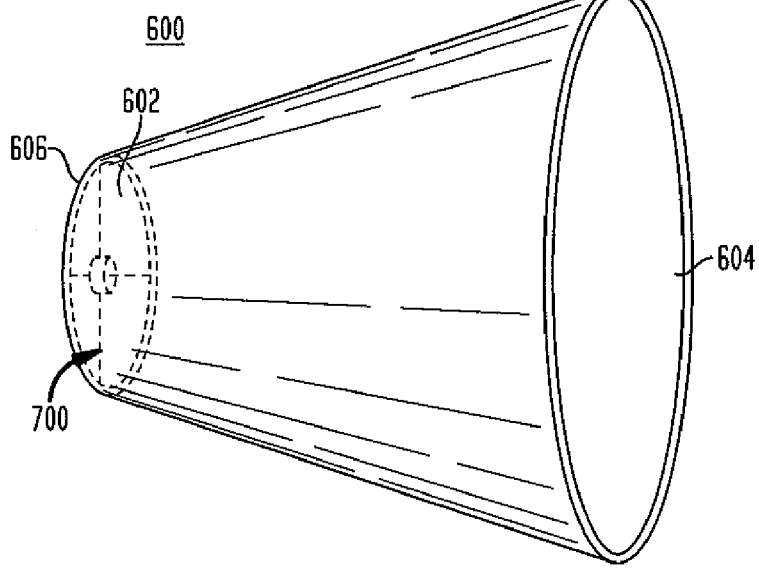
FIG. 6 is a perspective view of an alternative chamber of the present invention with an alternative sublimation system.
Figure 7:
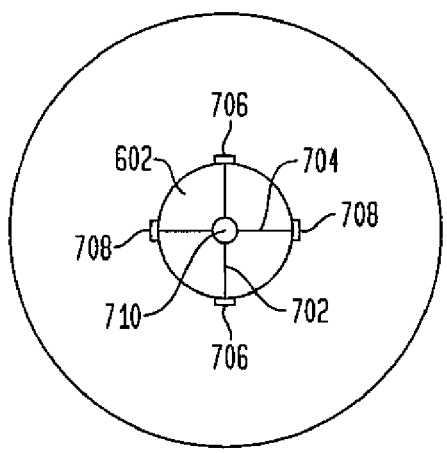
FIG. 7 is a planar bottom view of the alternative chamber with the alternative sublimation system.
Figure 8:
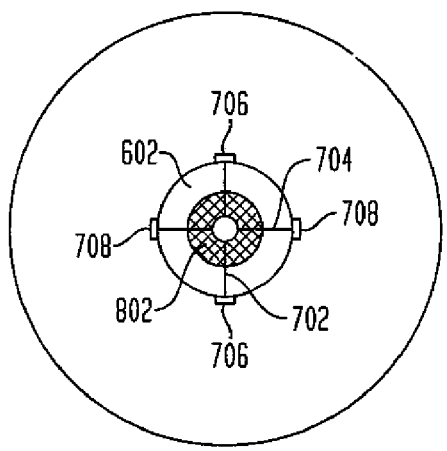
FIG. 8 is a planar bottom view of the alternative chamber with a second alternative sublimation system.

A third and fourth embodiment of the sublimation system 124 are shown in FIGS. 6-8 which also uses the chamber 402 shown in FIG. 4. A pair of tethers 702, 704 is connected to the edge 606 of the entry aperture 602 of a chamber 600 by mechanical fasteners 706, 708. The pair of tethers 702, 704 are each preferably a metal wire. In addition, a pair of tethers 702, 704 are used for convenience. It would be readily apparent to one of ordinary skill in the art to use one or more tethers, or a comparable means for securing the chamber 600 to a heat source 114.

In FIGS. 6 and 7, the sublimation systems 700, 800 further comprise a small porous pad 710, such as steel wool, secured to the intersection of the pair of tethers 702, 704. Alternatively, in FIG. 8, the sublimation system 800 further comprises a porous platform 802, such as a metal or plastic mesh screen, secured to the pair of tethers 702, 704 overlaying the intersection of the tethers 702, 704. Then, liquid or solid cyanoacrylate is deposited on the porous pad 710 or porous platform 802. In the case of a solid cyanoacrylate, e.g., in pellet form, the solid cyanoacrylate may be secured directly to the porous platform 802 by an adhesive, fastener, or in the curing process if the porous screen 802 is plastic. When the chamber 600 is mounted to the heat source 114, the heat emitting end 126 of the heat source 114 is aligned with and positioned immediate in front of the entry aperture 602 of the chamber 600, as well as, is preferably aligned with the porous pad 710.

In operation, upon activating the heat source 114, the heat engages the sublimation system 700, 800 and the heat transforms the cyanoacrylate into vapor within the chamber 600 thereby enabling the development of latent fingerprints.

Figure 9:
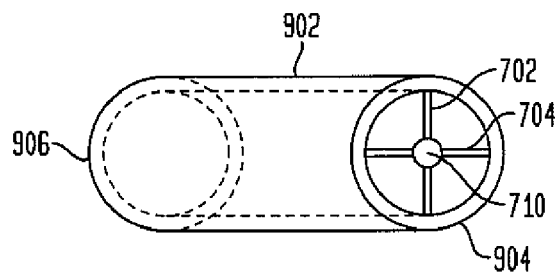
FIG. 9 is a perspective view of an alternative sublimation cartridge.

FIG. 9 is a perspective view of an alternative sublimation system 900 having a sublimation cartridge 902 having a first end 906 and a second end 904. The first end 906 is adapted to slidably attach to the heat emitting end 126 of the heat source 114. The second end 904 has the pair of tethers 702, 704 as shown in FIGS. 7 and 8. Also, shown is a porous pad 710 adapted to receive and retain the cyanoacrylate. Alternatively, a porous platform 802 may be incorporated into this sublimation cartridge 900 as described above. In operation, the sublimation cartridge 900 is used as also described above.

The evidence backlog in crime labs can extend to over a year. Thus, fingerprint processing may not occur until long after the crime has occurred, which impacts the integrity of the latent fingerprint. A particular challenge in visualizing older latent fingerprints is that the moisture content has evaporated resulting in a low rate of attachment of cyanoacrylate vapor to the fingerprint ridges.

In one embodiment an apparatus and method of rehydrating old latent fingerprints by increasing the hygroscopic potential of the old latent fingerprint comprises of treating the object or evidence to thermo cycling in a humidity controlled environment. As used herein temperature cycling or thermo cycling means to lower and raise the temperature of the environmental chamber in intervals to promote rehydration of the old latent fingerprint. Thermo cycling controls the rate of condensation thereby influencing rehydration of the latent fingerprint. While not intending to be bound to a particular theory, it is thought that thermo cycling expands water molecules, resulting in "cracking" or breaking of the 2% solid components of a latent fingerprint, which contributes to increasing the hygroscopic potential of the latent fingerprint.

Figure 15:
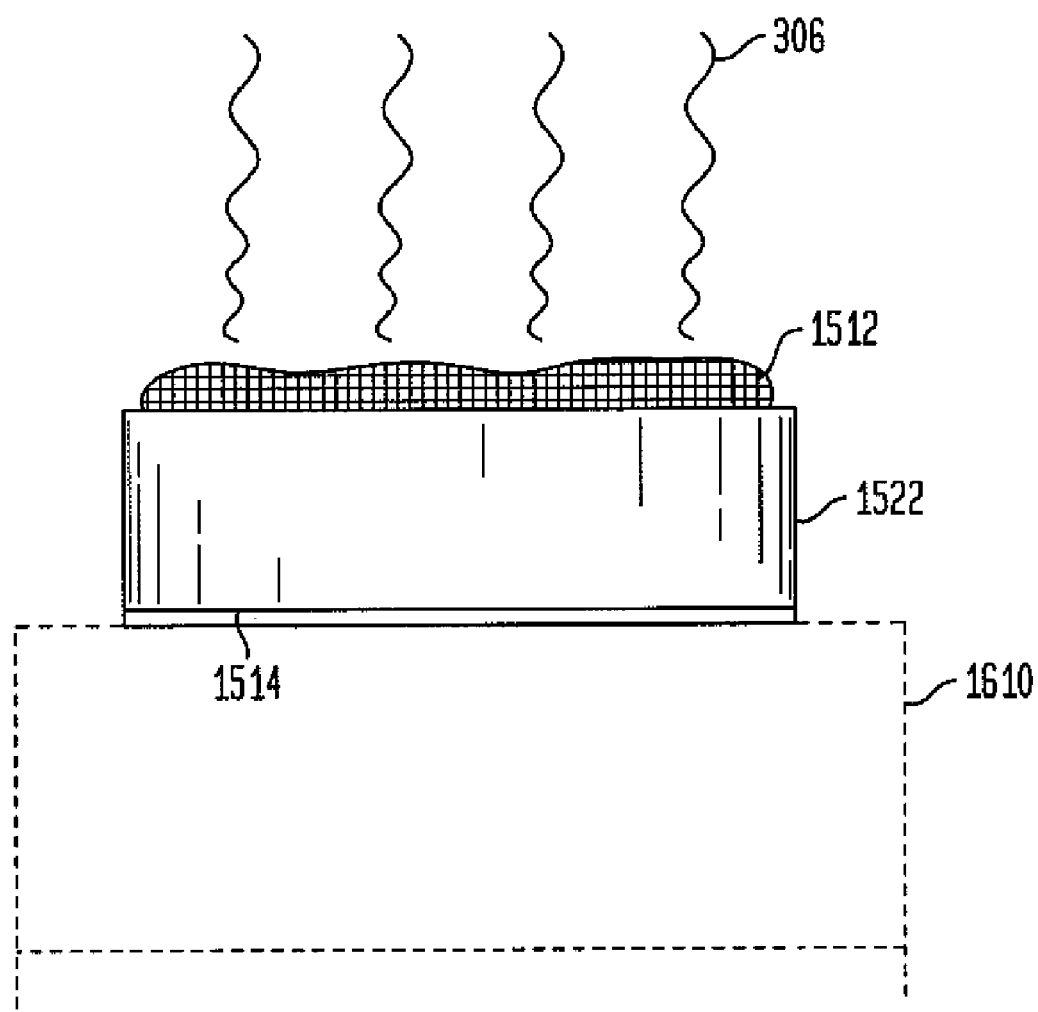
FIG. 15 is front view of an alternative sublimation cartridge.
Figure 16:
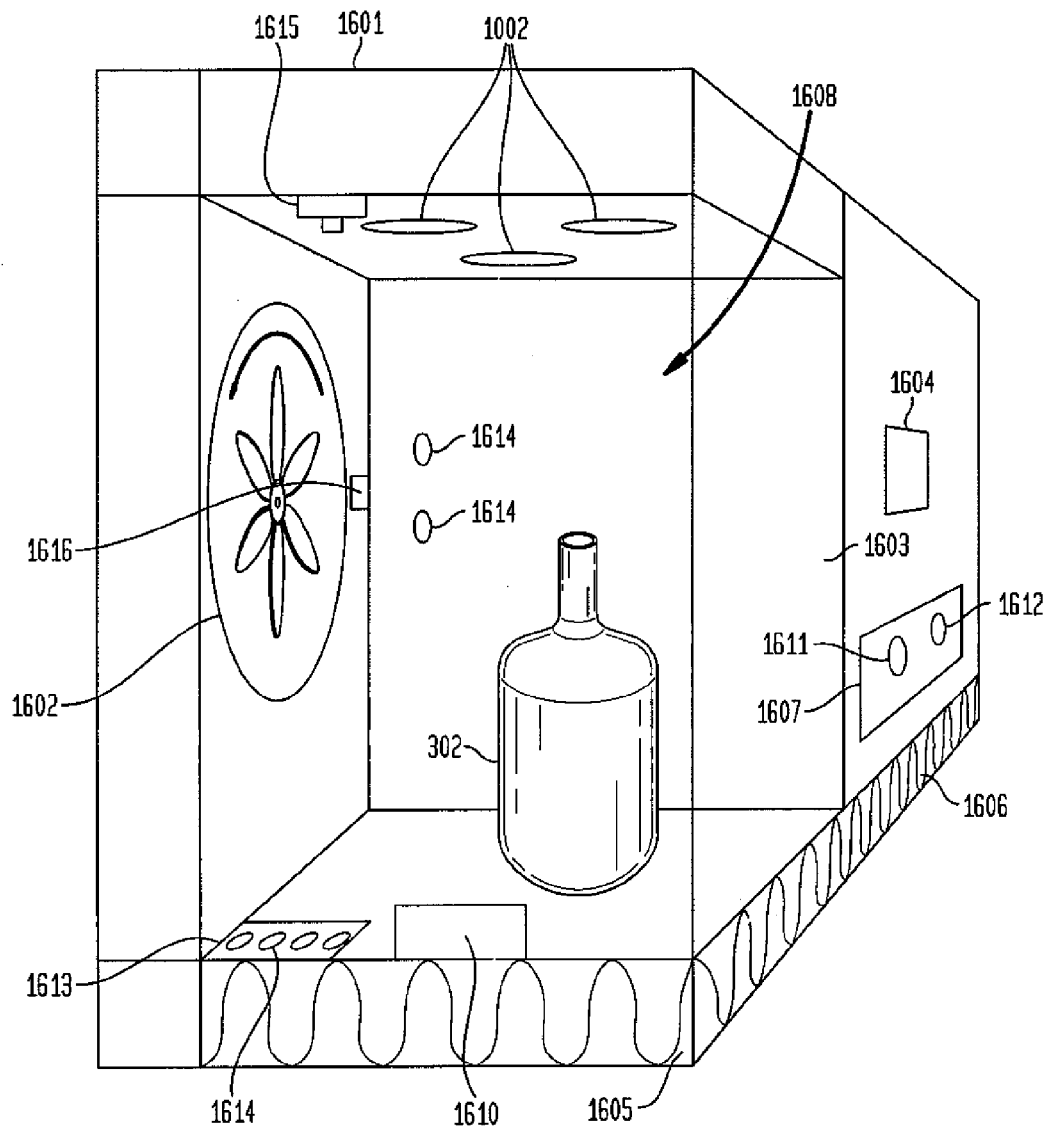
FIG. 16 is a perspective view of an alternative chamber of the present invention with an alternative sublimation system.

Referring to FIG. 15, an alternative embodiment of the sublimation cartridge 1522 is preferably made of metal, ceramic, or glass and is about 5-6 inches in length. The sublimation cartridge 1522 contains the components needed to create the cyanoacrylate vapors 306 used in developing latent fingerprints. In this first embodiment, a porous pad 1512, such as a ball of steel wool, ceramic fiber, granulated loose wool, and non-granulated loose wool, is disposed on bed 1514. Bed 1514 rests on or is in communication with the heating element 1610 located within chamber 1601, as depicted in FIG. 16. A mixture of liquid cyanoacrylate and/or sublimation dye is deposited on the porous pad 1512 and allowed to dry. Upon activation of heating element 1610, vapor 306 begins to develop.

Referring to FIG. 16, an alternative embodiment is apparatus 1600 which comprises an environmental chamber 1601. Chamber 1601 is a transparent chamber with an internal space 1608 for holding an object or evidence 302. In one embodiment, the chamber 1601 comprises a thermo cycling apparatus which comprises heating coils 1606 and/or cooling coils 1605. In one embodiment, the apparatus is controlled by a computer 1604 for automating the thermo cycling process. A computer and associated electronics control the temperature of interior space 1608 in accordance with the user supplied data defining the times, temperatures and number of cycles, etc. In one aspect the thermo cycling apparatus has a temperature profile of about 0° F. to about 250° F. In another embodiment, the temperature is controlled from within about 31° F. to about 98° F. Chamber 1601 further comprises the light source 1002, similar to light source 1002 as used in chamber 102. In another embodiment chamber 1601 comprises an integrated optical filter as used in chamber 102. In one embodiment the light source 1002 includes different frequency light sources 1002. In one aspect the light source 1002 is incorporated into at least one panel 1603 of chamber 1601.

Chamber 1601 further comprises a humidifying apparatus 1607, which in one embodiment includes a steam generator 1611. In one embodiment of the apparatus 1600, an inert gas, such as nitrogen gas is used to protect the fingerprints from oxidation and comprises a gas injection device 1612. The steam generator 1611 includes a source and the associated plumbing to allow for injection of steam into the interior space 1608. The gas injection device 1612 includes a source and the associated plumbing to allow injection of an inert gas into chamber 1601. In one embodiment the inert gas is nitrogen gas. In one embodiment humidifying apparatus 1607 has a humidity profile of ambient to zero humidity. A person of ordinary skill in the art that will recognize that other devices for increasing humidity or decreasing humidity can be substituted for humidifying apparatus 1607.

In a further embodiment, chamber 1601 comprises a light source 1002. In still another embodiment, chamber 1601 comprises a fan 1602 or any other means of circulating the inert gas and vapors 306 within the interior space 1608. In one aspect chamber 1601 comprises a compartment 1613 containing mobile fluffy balls 1614 made of porous light cloth-like material. A person of ordinary skill in the art will recognize that the introduction of steam and/or nitrogen gas will not only affect the humidity of the environment but also the temperature of the environment as well.

In one embodiment a process for enhancing fingerprint detection includes thermo cycling the interior 1608 to induce temperature inversion, which increases the hygroscopic potential of fingerprints deposited on porous and non-porous surfaces. In one aspect, temperature inversion includes lowering the temperature to about freezing temperature (31°-33° F.) and then raising the temperature to about near body temperature (98° F.) in a low humidity environment. In one embodiment the thermo cycling process is repeated for at least 2 cycles. In another embodiment the thermo cycling process is repeated for about 3 to 6 cycles. In still a further embodiment the thermo cycling process is repeated for about 5 to 9 cycles. In one aspect the low temperature (about freezing point in one embodiment) is held for about 1 to about 30 minutes or for a sufficient time to induce rehydration of the latent fingerprint as would be readily determined by a person of ordinary skill in the art. In another aspect the high temperature (about body temperature in one embodiment) is held for about 1 to about 30 minutes or for a sufficient time to induce rehydration of the latent fingerprint as would be readily determined by a person of ordinary skill in the art. In one embodiment, the humidity is about zero percent. In another embodiment, the humidity is cycled from about zero percent to about ambient humidity in unison with thermo cycling.

In another aspect the thermo cycling influences the rate of fingerprint development by enhancing the attachment of cyanoacrylate vapor to the latent fingerprint. For example, seven times more by weight cured cyanoacrylate polymer was achieved at 45° F. compared to 83° F.

In one aspect, light source 1002 is a UV emitting source. In one embodiment, the object is exposed to UV light during the polymerization process of the cyanoacrylate vapor to enhance the finger print development.

The use and operation of an alternative embodiment of the present invention is the apparatus 1600, as shown in FIG. 16. A user (not shown) activates the thermo cycling apparatus, via the computer 1604 (by entering the user defined parameters such as temperature, time, number cycles etc.). The thermo cycling apparatus cools the temperature in the chamber 1601 to about 31° F. and keeps the temperature steady for 1 to about 30 minutes or for a sufficient time to induce rehydration of the latent fingerprint as would be readily determined by a person of ordinary skill in the art. Optionally, the light source 1002, emitting UV light, is activated once the chamber 1601 reaches the low temperature. Then the thermo cycling apparatus raises the temperature in the chamber 1601 to about 98° F. and keeps the temperature steady for 1 to about 30 minutes or for a sufficient time to induce rehydration of the latent fingerprint as would be readily determined by a person of ordinary skill in the art. The cycling is repeated, in some embodiments for 2 to about 8 times, or for the number of cycles sufficient to induce rehydration of the latent fingerprints as would be readily determined by a person of ordinary skill in the art. Concurrently, the humidity control apparatus 1607, which in one embodiment includes, steam generation device 1611 and gas injection device 1612 is activated to lower the humidity to about zero percent. In another embodiment the humidity is cycled from about zero percent to about ambient humidity. In another embodiment the gas injection device 1612, which in one embodiment uses nitrogen gas, is activated prior to thermo cycling to purge the interior space 1608.

The user then activates the heat element 1610 to heat the mixture of cyanoacrylate and/or sublimation dye disposed on the porous pad 1512 which in turn generates vapors 306, which is comprised of cyanoacrylate and/or sublimation dye vapors. The vapors 306, with the aid of fan 1602, containing cyanoacrylate and/or sublimation dye attach to latent fingerprints. Latent fingerprints start to develop within seconds because chamber 1601 contains the vapors 306 within the internal space 1608 and directs the vapors 306 directly toward and around the object. In one aspect, activation of fan 1602 sets in motion fluffy balls 1614 held in compartment 1613, which enhances the distribution vapors 306 onto object 1609.

The user then activates the light source 1002. In the embodiment depicted, multiple light sources 1002 are used in combination. In other embodiments, a light source 1002 is used to emit light to stimulate or excite the sublimation dye. The photoluminescent emissions associated with the sublimation dye enhances the visibility of the developed fingerprints which are observed by looking through chamber 1601, which in one embodiment has appropriate optical filtering integral with panel 1603. Alternatively, the photoluminescence is captured by the capture device 1616. In an alternative embodiment, the user removes the object 302 with the developed fingerprint and examines the developed fingerprints under appropriate wavelength light by using goggles with appropriate optical filtering. In one embodiment, goggles with appropriate optical filtering adapted to the sublimation dye, and with integrated LEDs used to stimulate the sublimation dye, are used to view the developed latent fingerprints.

Figure 17:
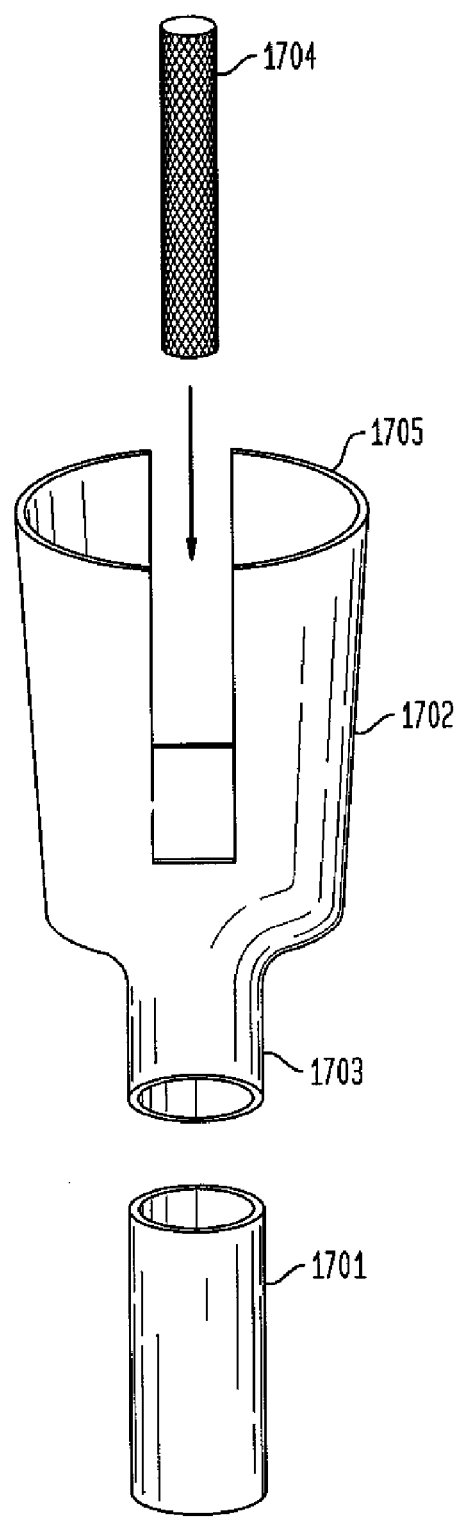
FIG. 17 is a perspective view of an alternative sublimation cartridge of the apparatus.

In another embodiment, an alternative sublimation cartridge 1700 is depicted in FIG. 17. Sublimation cartridge 1700 comprises a heat emitting adaptor 1701 which can slide onto a heat emitting end of a heat source 114. Attached to heat emitting adaptor 1701 is the sublimation canister 1702, made from a high temperature resistant material, non limiting examples include: brass, metal, ceramics, composites etc. Sublimation canister 1702 is adapted to receive a removable and disposable sublimation wafer 1704. Sublimation wafer 1704 is designed to be disposable and/or recharged after every use. Sublimation wafer 1704 is impregnated with cyanoacrylate alone or in combination with a sublimation dye such as yellow 43. Upon activation of a heat source, vapors 306 begin to develop and in one embodiment, output end 1705 is directed into chamber 1601 to surround object 1609 with vapors 306.

In one embodiment, as depicted in FIG. 18, a filter goggles 1800 is worn by the user (not shown) during the forensic investigation/examination of evidence. In one embodiment, an optical filter 1802 is built-into the lens of filter goggles 1800 to pass/transmit photoluminescent emissions produced by the sublimation dye after excitation from a light source, while attenuating light not associated with the photoluminescent emissions. In another embodiment the filter goggles 1800 is used to view objects contained in chamber 102. In this embodiment, the object 302 is placed in chamber 102 and vapor 306 is allowed to condense onto the object. Object 302 is then viewed with the filter goggles 1800 while contained in chamber 102. In another embodiment object 302 is removed from chamber 102 and viewed with the filter goggles 1800. In another embodiment, shown in FIG. 18, the vapor 306 is fumed onto the object 302, such as with the apparatus 400, without chamber 102 and subsequently viewed with the filter goggles 1800.

In one embodiment, the filter goggles 1800 contains an optical filter 1802 made of amber colored acrylic plastic which attenuates scattered blue excitation light to further enhance the detection of the photoluminescent emissions from the developed fingerprint. A person of ordinary skill in the art would recognize that the filter goggles 1800 can be adjusted to pass/transmit the desired range of wavelength.

In one embodiment, the filter goggles 1800 passes photoluminescent emissions occurring at least in one of the following ranges: about 75 nm to about 380 nm, about 380 nm to about 450 nm, about 435 nm to about 445 nm, about 450 nm to about 495 nm, about 495 nm to about 570 nm, about 515 nm to about 540 nm, about 570 nm to about 590 nm, about 590 nm to about 620 nm, about 620 nm to about 750 nm, about 750 nm to about 1000 nm, about 1000 nm to about 1250 nm, about 1250 nm to about 1500 nm, about 1500 to about 3000 nm, and about 3000 nm to about 10,000 nm.

In another embodiment, the optical filter 1802 contained in the filter goggles 1800 is constructed from a colored transparent acrylic plastic such as Acrylite® amber (Cyro#436-4 GP or Chemcast #2422) available from CYRO Industries. Non-limiting examples of colored acrylic plastic include yellow, blue, green, red, bronze, gray, pink and burgundy.

In still a further embodiment, narrow band pass filters are mounted to the filter goggles 1800 with rotational functionality. The narrow band pass filter element is adapted to change the transmission properties of the optical filter 1802 based on the rotation of the narrow band pass filters (i.e. by rotating a more or less transmissive filter in or out of the field of view of the user). The narrow band pass filters are adjusted rotationally to bring varying filters into the user's field of view, allowing the user to modulate the filtering of the light. In one embodiment the narrow band pass filters are adjustable to within +/−10 nm range of a wavelength. In another embodiment the narrow band pass filters are adjustable to within +/−(10 nm-150 nm) range of a wavelength.

In another embodiment one or more wavelength specific LED light sources 1806 are mounted onto the filter goggles 1800. In one aspect the filter goggles 1800 is powered by an electric power source, non-limiting examples include batteries or direct current modified to specific voltages or power conditioning functions. In another aspect the LED light source 1806 has variable movement and focus functionality allowing the user to select for a wide dispersion of light or a more focused/concentrated dispersion of light. In another aspect the LED light source 1806 contains filter inserts as understood by a person of ordinary skill in the art. A non-limiting example of filter inserts include rotatable polarization filters which allow for refinement in detection sensitivity through adjustment of the polarization angle by polarization lever 1808. It is well known in the art that visualization of blood stains or blood splatter can be enhanced with the application of polarized light. In one embodiment, blood stains or blood splatter is illuminated by polarized light from LED source 1806 and viewed with filter goggles 1800.

In still a further embodiment, the filter goggles 1800 includes rotatable polarization filters allowing for adjustment in polarization angle by polarization lever 1804. It is well known in the art that polarized filters can reduce unwanted reflections. In one embodiment polarization lever 1804 of filter goggles 1800 is adjusted when viewing photoluminescent emissions from reflective surfaces such as mirrors, metal or glass surfaces. In another embodiment, the polarization filter is adapted to be flipped up or removed from filter goggles 1800.

In another embodiment narrow band pass filters with integral polarization filters are mounted to the filter goggles 1800 with rotational functionality. The narrow band pass filters are adjusted rotationally which restricts the wavelength of light passed/transmitted, resulting in increased detection sensitivity. In one embodiment the narrow band pass filters are adjustable to within +/−10 nm range of a wavelength. In another embodiment the narrow band pass filters are adjustable to within +/−(10 nm-150 nm) range of a wavelength.

In one embodiment the LED light source 1806 emits light in a range from about 415 nm to about 505 nm. In still another embodiment, the LED light source 1806 emits a substantial portion of its light in a range from about 415 nm to about 505 nm. In still another embodiment, the LED light source 1806 emits substantially all of its light within a +/−10 nm range of a wavelength selected from between 415 nm and 505 nm. In another embodiment the LED light source 1806 is a blue LED emitting light between a range of about 450 nm and 470 nm.

In one embodiment the LED light source 1806 has variable wavelength functionality and emits light in at least one of the following ranges: ultra violet spectrum, visible light spectrum or the infra-red spectrum. In one embodiment, the LED light source 1806 emits a substantial portion of its light in at least one of the following ranges: about 75 nm to about 380 nm, about 380 nm to about 450 nm; about 450 nm to about 495 nm; about 495 nm to about 570 nm; about 570 nm to about 590 nm; about 590 nm to about 620 nm, about 620 nm to about 750 nm, about 750 nm to about 1500 nm, about 1500 nm to about 3000 nm and about 3000 nm to about 10,000 nm. In yet another embodiment, the LED light source emits the majority of its radiation within +/−10 nm range of 450 nm.

CONCLUSION

While various embodiments of the present invention have been described above, it should be understood that they have been presented by the way of example only, and not limitation. It will be understood by those skilled in the art that various changes in form and details may be made therein without departing from the spirit and scope of the invention as defined. Thus, the breadth and scope of the present invention should not be limited by any of the above-described exemplary embodiments.

What is claimed is:

1. An apparatus for developing latent fingerprints on an object, comprising:
    a vapor comprising a sublimation dye and a cyanoacrylate;
    wherein said vapor condenses at least in part on the object;
    a light source adapted with a variable wavelength emission functionality to excite said vapor deposited on the object; and
    a filter goggle with an optical filter adapted with a variable wavelength filtering functionality to pass a photoluminescent emission associated with said sublimation dye.

2. The apparatus of claim 1, further comprising:
    a narrow band pass filter element adapted to modulate wavelength filtering of said optical filter.

3. The apparatus of claim 2, wherein said narrow band pass filter element is adapted to modulate within a +/−10 nm range of a wavelength.

4. The apparatus of claim 2, wherein said narrow band pass filter element is adapted to modulate within a +/−10 nm to 150 nm range of a wavelength.

5. The apparatus of claim 1, wherein said optical filter includes a rotatable polarization filter.

6. The apparatus of claim 1, wherein said light source is adapted to vary wavelength emission of a majority of said light source's radiation in a range from about 415 nm to about 505 nm.

7. A goggle apparatus for fingerprint detection, comprising:
    a light source adapted with a variable wavelength emission functionality to excite a vapor deposited on an object, wherein said vapor comprises a sublimation dye; and
    an optical filter adapted with a variable wavelength filtering functionality to pass a photoluminescent emission associated with said sublimation dye.

8. The goggle apparatus of claim 7, further comprising:
    a narrow band pass filter element adapted to modulate wavelength filtering of said optical filter.

9. The goggle apparatus of claim 8, wherein said narrow band pass filter element is adapted to modulate within a +/−10 nm range of a wavelength.

10. The goggle apparatus of claim 8, wherein said narrow band pass filter element is adapted to modulate within a +/−10 nm to 150 nm range of a wavelength.

11. The goggle apparatus of claim 7, wherein said optical filter includes a rotatable polarization filter.

12. The goggle apparatus of claim 7, wherein said light source is adapted to vary wavelength emission of the majority of its radiation in a range from about 415 nm to about 505 nm.

13. The goggle apparatus of claim 7, wherein said light source is adapted to vary wavelength emission of a majority of said light source's radiation in a range from about 415 nm to about 505 nm.

14. A goggle apparatus for fingerprint detection, comprising:
    a light source adapted to excite a vapor deposited on an object, wherein said vapor comprises a sublimation dye; and
    an optical filter adapted with a variable wavelength filtering functionality to pass a photoluminescent emission associated with said sublimation dye.

15. The goggle apparatus of claim 14, further comprising:
    a narrow band pass filter element adapted to modulate wavelength filtering of said optical filter.

16. The goggle apparatus of claim 15, wherein said narrow band pass filter element is adapted to modulate within a +/−10 nm range of a wavelength.

17. The goggle apparatus of claim 15, wherein said narrow band pass filter element is adapted to modulate within a +/−10 nm to 150 nm range of a wavelength.

18. The goggle apparatus of claim 14, wherein said optical filter includes a rotatable polarization filter.

19. The goggle apparatus of claim 14, wherein said light source is adapted to vary wavelength emission of a majority of said light source's radiation in a range from about 415 nm to about 505 nm.

20. The goggle apparatus of claim 14, wherein said light source is adapted to emit the majority of its radiation within a +/−10 nm range of 450 nm.

* * * * *